United States Patent
Scheiner et al.

(10) Patent No.: US 9,370,654 B2
(45) Date of Patent: Jun. 21, 2016

(54) HIGH FREQUENCY STIMULATION TO BLOCK LARYNGEAL STIMULATION DURING VAGAL NERVE STIMULATION

(75) Inventors: Avram Scheiner, Vadnais Heights, MN (US); David E. Euler, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1781 days.

(21) Appl. No.: 12/360,680

(22) Filed: Jan. 27, 2009

(65) Prior Publication Data
US 2010/0191311 A1    Jul. 29, 2010

(51) Int. Cl.
   *A61N 1/05*      (2006.01)
   *A61N 1/36*      (2006.01)
   *A61B 5/00*      (2006.01)

(52) U.S. Cl.
CPC .......... *A61N 1/0556* (2013.01); *A61B 5/4047* (2013.01); *A61N 1/36114* (2013.01); *A61B 5/4035* (2013.01); *A61B 5/7217* (2013.01)

(58) Field of Classification Search
CPC .................. A61N 1/0556; A61N 1/36114
USPC ................. 607/48, 62, 66, 69–72, 118
See application file for complete search history.

(56) References Cited

U.S. PATENT DOCUMENTS

| | | | |
|---|---|---|---|
| 6,418,346 B1 | 7/2002 | Nelson et al. | |
| 6,865,419 B2 | 3/2005 | Mulligan | |
| 7,277,761 B2 | 10/2007 | Shelchuk | |
| 7,617,003 B2 | 11/2009 | Caparso et al. | |
| 7,672,727 B2 * | 3/2010 | Donders et al. | 607/40 |
| 7,783,362 B2 | 8/2010 | Whitehurst et al. | |
| 8,165,681 B2 | 4/2012 | King | |
| 8,798,754 B2 | 8/2014 | Knudson et al. | |
| 2002/0055779 A1 | 5/2002 | Andrews | |
| 2003/0236558 A1 | 12/2003 | Whitehurst et al. | |
| 2004/0172085 A1 | 9/2004 | Knudson et al. | |
| 2005/0070970 A1 | 3/2005 | Knudson et al. | |
| 2005/0070974 A1 * | 3/2005 | Knudson et al. | 607/58 |
| 2005/0131486 A1 | 6/2005 | Boveja et al. | |
| 2005/0143787 A1 | 6/2005 | Boveja et al. | |
| 2005/0149148 A1 * | 7/2005 | King | 607/70 |
| 2006/0020293 A1 * | 1/2006 | Euler | 607/14 |
| 2006/0079936 A1 | 4/2006 | Boveja et al. | |
| 2006/0149337 A1 | 7/2006 | John | |
| 2006/0293723 A1 * | 12/2006 | Whitehurst et al. | 607/48 |
| 2007/0067004 A1 | 3/2007 | Boveja et al. | |
| 2007/0073357 A1 | 3/2007 | Rooney et al. | |
| 2008/0021512 A1 | 1/2008 | Knudson et al. | |
| 2008/0058871 A1 | 3/2008 | Libbus et al. | |

(Continued)

OTHER PUBLICATIONS (PCTUS2010/0234780) PCT Notification of Transmittal of the International Search Report and the Written Opinion of the International Searching Authority, 13 pages.

Taic C, Block of external urethral sphincter contraction by high frequency electrical stimulation of pudendal nerve, Urol., 172:2069-2072, 2004.

(Continued)

*Primary Examiner* — Catherine Voorhees
(74) *Attorney, Agent, or Firm* — Carol F. Barry (57) ABSTRACT

An implantable medical device and associated method deliver a therapy to an autonomic nerve. The therapy delivery includes delivering therapeutic low frequency (LF) electrical stimulation pulses to the autonomic nerve and delivering a high frequency electrical signal to the autonomic nerve during the LF frequency stimulation pulse delivery. The high frequency stimulation signal blocks activation of autonomic nerve fibers innervating a non-targeted tissue during the therapeutic LF stimulation pulse delivery.

14 Claims, 8 Drawing Sheets

(56) References Cited

U.S. PATENT DOCUMENTS

| | | |
|---|---|---|
| 2008/0058874 A1 | 3/2008 | Westlund et al. |
| 2008/0132964 A1 | 6/2008 | Cohen et al. |
| 2008/0147137 A1 | 6/2008 | Cohen et al. |
| 2008/0234780 A1 | 9/2008 | Smith et al. |
| 2009/0275855 A1* | 11/2009 | Zielinski et al. .............. 600/547 |

OTHER PUBLICATIONS

Bhadra N, High frequency electrical conduction block of mammalian peripheral motor nerve., Muscle Nerve, 32:782-790, 2005.

Kilgore KL, Nerve conduction block utilizing high-frequency alternating current., Med Biol Eng Comput., 42:394-406, 2004.

Bhadra N, High frequency electrical conduction block of the pudendal nerve., Neural Eng 3:180-187, 2006.

Tai C, Simulation analysis of conduction block in unmyelinated axons induced by high frequency biphasic electrical currents. IEEE Trans Biomed Eng., 52:1323-1332, 2005.

Bhadra N, Simulation of high frequency sinussoidal electrical block of mammalian myelinated axons., J Comput Neurosci., 22:313-326, 2007.

Cohn AE, The predominant influence of the left vagus nerve upon conduction between the auricles and the ventricles in the dog., J Exp Med., 18:739-747, 1913.

Rinkema LE, Effects of individual cardiac nerve stimulation on atrioventricular conduction., J Auton Nerv Sust., 5:357-371, 1982.

Kralios FA, Local ventricular repolarization changes due to sympathetic nerve-branch stimulation., Am J Physiol., 228:1621-1626, 1975.

Norris JE, Responses of the canine myocardium to stimulation of thoracic cardiac nerves. Am J Physiol., 232:H485-H494, 1977.

Banks AP, High strength stimulation of the vagus nerve in awake humans: a lack of cardiorespiratory effects., Respir Physiol., 127:125-133, 2001.

Spelman FA, Continuous measurement of renal cortical blood flow and renal arterial blood flow during stimulation of the renal nerve. Med Biol Eng Comput. 29:121-128, 1991.

\* cited by examiner

HIGH FREQUENCY STIMULATION TO BLOCK LARYNGEAL STIMULATION DURING VAGAL NERVE STIMULATION

TECHNICAL FIELD

The invention relates generally to implantable medical devices and, in particular, to delivering high frequency (HF) blocking stimulation during therapeutic stimulation for autonomic nerve activation.

BACKGROUND

Vagal nerve stimulation slows the heart rate and is promising as a cardiac therapy in the treatment of arrhythmias and heart failure. The stimulation activates the cardiac branches of the vagus nerve which innervate the sinus node, thereby causing slowing a sinus rate. The vagus nerve, however, has many other branches which are not targeted for activation during vagal nerve stimulation intended as a cardiac therapy. Among the vagus nerve branches are those innervating the pharynx and the larynx. Undesired side effects that can occur with vagal nerve stimulation intended as a cardiac therapy include shortness of breath, voice alteration, hoarseness, neck pain, and coughing caused by undesired activation of the non-cardiac vagus nerve branches in response to vagus nerve stimulation pulses.

DETAILED DESCRIPTION

In the following description, references are made to illustrative embodiments. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Embodiments described herein relate primarily to vagus nerve stimulation for achieving a beneficial cardiac effect. Apparatus and methods described herein, however, may be adapted for use in other autonomic nerve stimulation applications. As will be described, a low frequency therapeutic stimulation is delivered for activating autonomic nerve fibers innervating a targeted tissue for achieving a therapeutic effect. During the low frequency therapeutic stimulation, a high frequency (HF) blocking stimulation is also delivered to the vagus nerve to reduce the likelihood of activating (i.e. depolarizing) nerve fibers innervating non-targeted tissues. It is recognized that the combination of therapeutic activation and blocking stimulation as described herein can be implemented in other therapy delivery applications involving electrical stimulation of autonomic nerves.

As used herein, the term "high frequency" with regard to blocking stimulation refers to a frequency greater than a maximum frequency at which nerve fiber depolarization can occur, regardless of an applied pulse amplitude. Effective HF blocking stimulation is expected to be at least 1 kHz in contrast to therapeutic stimulation delivered at frequencies intended to activate or depolarize a targeted tissue. The frequency of therapeutic stimulation is typically less than 100 Hz, and more typically in the range of up to about 50 Hz. As such, there is expected to be at least a 10-fold difference, and possibly a 100 or even 1,000-fold difference, between the LF therapeutic stimulation and the HF blocking stimulation.

Figure 1:
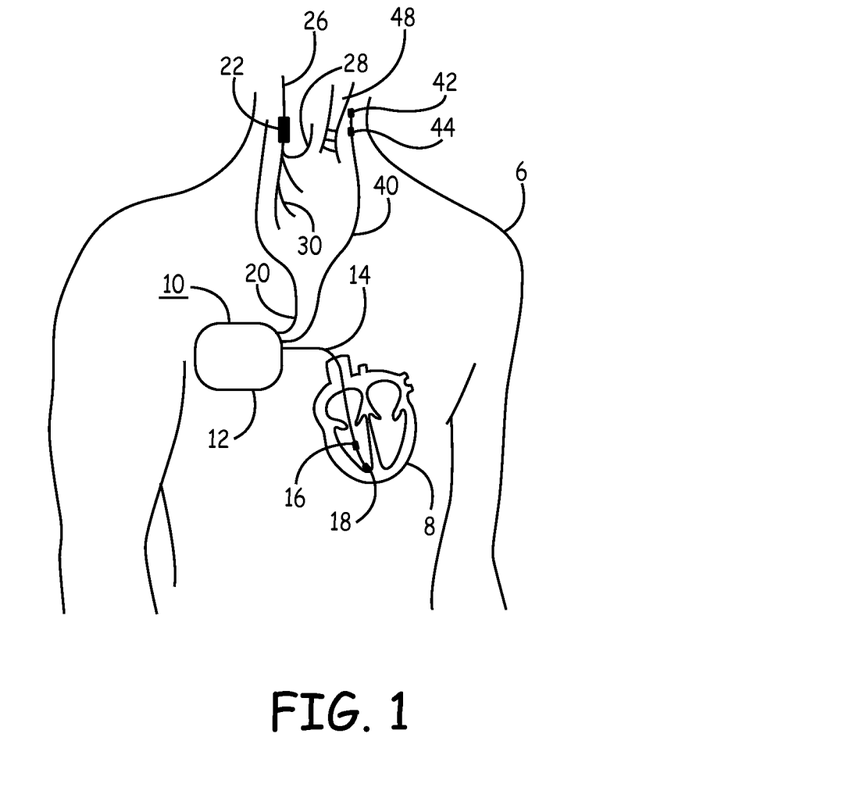
FIG. 1 is a schematic diagram of an implantable medical device system for delivering vagal nerve stimulation to achieve a therapeutic cardiac effect.

FIG. 1 is a schematic diagram of an implantable medical device system for delivering vagal nerve stimulation to achieve a therapeutic cardiac effect. Implantable medical device (IMD) 10 is shown implanted in a patient's body 6 in operative relation to the patient's heart 8 and vagus nerve 26. A cardiac lead 14 is coupled to IMD 10 and extends to the patient's heart 8 to position one or more electrodes 16 and 18 in or along heart 8. Electrodes 16 and 18 are shown as intracardiac electrodes that may be used in sensing the heart rate for determining a need for therapy delivery or therapy adjustment. Electrodes 16 and 18 may also be used in delivering cardiac stimulation therapies directly to the heart 8. Electrodes 16 and 18 may be used in combination with housing 12 of IMD 10. Housing 12 is typically hermetically sealed and encloses the circuitry of IMD 10. It is recognized that lead 14 may alternatively or additionally include other types of physiological sensors such blood pressure sensors, impedance measuring electrodes, or accelerometers for use in monitoring cardiac function.

IMD 10 is coupled to a lead 20 extending toward the vagus nerve 26 for positioning a nerve cuff 22 along the vagus nerve 26 in the cervical region. Nerve cuff 22 carries at least one bipolar electrode pair (not shown). As will be explained herein, an electrode pair is used to deliver therapeutic stimulation pulses to cause excitation of a cardiac branch 30 of the vagus nerve 26. The same or another electrode pair is used to deliver high frequency blocking stimulation to block the excitation of non-cardiac vagus nerve branches 28, such as the laryngeal branches of the vagus nerve.

In some embodiments, IMD 10 may be further coupled to a lead 40 carrying one or more sensors 42 and 44 for detecting activation of the laryngeal muscles. Sensors 42 and 44 are positioned in the region of the larynx 48 for sensing intrinsic and/or evoked laryngeal activation. In one embodiment, sensors 42 and 44 are electrodes for sensing EMG signals. In other embodiments, a sensor carried by lead 40 may be a motion sensor such as an accelerometer or strain gauge, or an acoustical sensor such as a microphone. It is further recognized that sensors 42 and 44 deployed in operative relation to larynx 48 may be wireless sensors capable of transmitting sensed signal data to IMD 10.

Figure 2:
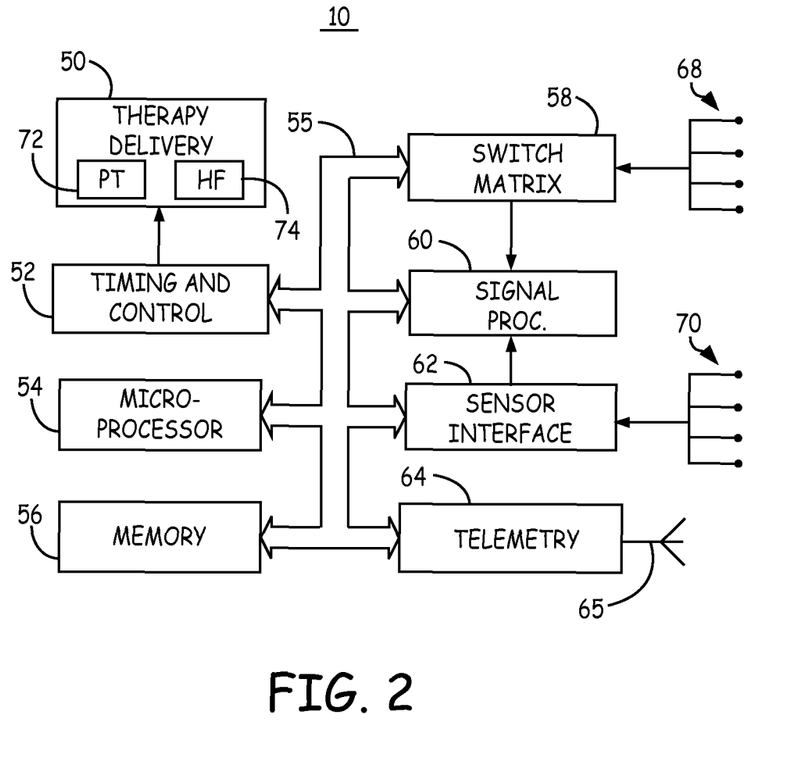
FIG. 2 is a functional block diagram of one embodiment of the IMD shown in FIG. 1.

FIG. 2 is a functional block diagram of one embodiment of IMD 10. IMD 10 generally includes timing and control circuitry 52 and an operating system that may employ microprocessor 54 or a digital state machine for timing sensing and therapy delivery functions in accordance with a programmed operating mode. Microprocessor 54 and associated memory 56 are coupled to the various components of IMD 10 via a data/address bus 55.

IMD 10 includes therapy delivery module 50 for delivering a therapy in response to determining a need for therapy based on sensed physiological signals or in response to IMD 10 receiving an external programming command. Therapy delivery module 50 provides electrical stimulation therapy and may provide other therapies such as drug delivery. In particular, therapy delivery module is configured for delivering therapeutic stimulation pulses to the vagus nerve for achieving a beneficial cardiac effect.

Therapy delivery module 50 includes a pulse train generator 72 for generating a relatively low frequency (LF) train of stimulation pulses for activating cardiac nerve branches to cause a cardiac response. Therapy delivery module 50 further includes a high frequency, alternating current (AC) signal generator 74 for delivering a relatively higher frequency stimulation waveform to the vagus nerve. The HF stimulation is delivered to cause a blocking response in non-cardiac vagus nerve fibers. In particular, the HF blocking stimulation is provided to cause blocking of vagus nerve branches innervating the laryngeal muscles.

Therapies are delivered by module 50 under the control of timing and control 52. Therapy delivery module 50 is coupled to one pair of electrodes selected from electrodes 68 for delivering LF therapeutic vagal stimulation for achieving a cardiac benefit and the same or another pair of electrodes 68 for delivering HF blocking stimulation to the vagus nerve. Electrodes coupled to therapy delivery module 50 may be selected via an optional switch matrix 58, allowing different electrode pairs positioned along the vagus nerve to be selected for different types of stimulation or to optimize a blocking or therapeutic stimulation response. Switch matrix 58 may be used for selecting which electrodes and corresponding polarities are used for delivering vagal nerve therapeutic stimulation and vagal nerve blocking stimulation. Electrodes 68 may be carried by a nerve cuff as shown in FIG. 1. Electrodes 68 may further include one or more cardiac electrodes, such as intracardiac electrodes 16 and 18 shown in FIG. 1, electrodes 42 and 44 (FIG. 1) positioned along the larynx, an electrode incorporated in IMD housing 12 (FIG. 1) or other lead-based electrodes, including subcutaneous electrodes.

Electrodes 68 may also be used for receiving electrical signals for sensing physiological events. In one embodiment, electrodes 68 include intracardiac electrodes 16 and 18 as shown in FIG. 1 for monitoring cardiac electrical signals for determining when a vagal stimulation therapy is needed or when adjustments to stimulation parameters are required. Electrodes 68 may further include laryngeal sensing electrodes 42 and 44 for sensing laryngeal activation. When used for sensing, electrode terminals 68 are coupled to signal processing circuitry 60 via switch matrix 58. Signal processor 60 includes sense amplifiers and may include other signal conditioning circuitry and an analog-to-digital converter. Electrical signals may then be used by microprocessor 54 for detecting cardiac events, determining a heart rate and detecting and discriminating cardiac arrhythmias. Electrodes 68 may further provide microprocessor 54 EMG signals for verifying HF blocking stimulation effectiveness or detecting intrinsic laryngeal activations.

IMD 10 may additionally be coupled to one or more physiological sensors 70. Physiological sensors 70 may include pressure sensors, motion sensors, acoustical sensors, flow sensors, blood chemistry sensors, activity sensors or other physiological sensors used for monitoring a physiological condition. Physiological sensors may be carried by leads extending from IMD 10 or incorporated in or on the IMD housing 12. A physiological sensor 70 coupled to IMD 10 may be positioned along a laryngeal muscle for detecting activations of the larynx, including intrinsic activations or evoked activations caused by vagal nerve stimulation. Physiological sensors appropriate for detecting laryngeal activations include motion sensors such as accelerometers or acoustical sensors such as microphones. Acoustical sensors may be used to detect muscle sounds associated with laryngeal activation or voiced sounds within the larynx.

Signals received at sensor terminals 70 are received by a sensor interface 62 which provides sensor signals to signal processing circuitry 60. Sensor signals are used by microprocessor 54 for detecting physiological events or conditions. In one embodiment, sensors 70 are used for monitoring a heart failure condition for detecting a need for vagal stimulation. Examples of heart failure monitoring using an implantable medical device are generally described in U.S. Pat. No. 6,865,419 (Mulligan), hereby incorporated herein by reference in its entirety.

The operating system includes associated memory 56 for storing a variety of programmed-in operating modes and parameter values that are used by microprocessor 54. The memory 56 may also be used for storing data compiled from sensed signals and/or relating to device operating history for telemetry out on receipt of a retrieval or interrogation instruction. Parameters used for controlling the delivery of vagus nerve stimulation are stored in memory 56.

IMD 10 further includes telemetry circuitry 64 and antenna 65. Programming commands or data are transmitted during uplink or downlink telemetry between IMD telemetry circuitry 64 and external telemetry circuitry included in a patient hand-held device, programmer, monitoring unit or other external device capable of bidirectional communication with IMD 10.

Figure 3A:
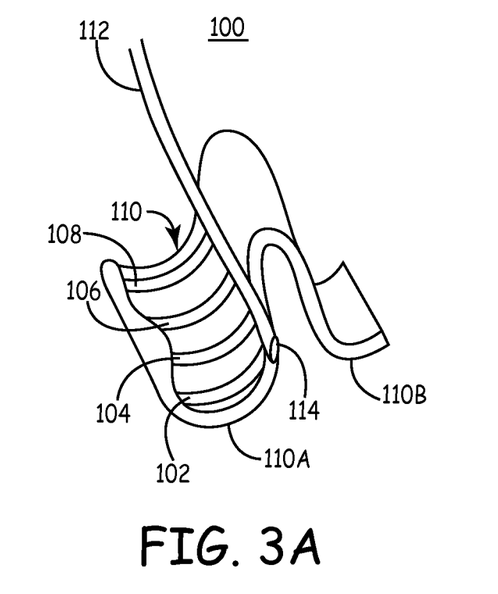
FIG. 3A is an illustration of a nerve cuff lead for use in delivering vagal nerve stimulation.

FIG. 3A is an illustration of a nerve cuff lead 100 for use in delivering vagal nerve stimulation. Lead 100 includes a nerve cuff 110 which may include two opposing flexible portions 110A and 110B for gently securing around the vagus nerve. As used herein, the term "distal" with respect to lead 100 refers to a location relatively closer to distal end 114 of lead 100. The term "proximal" with respect to lead 100 refers to a location relatively further away from distal end 114. A first pair of electrodes 102 and 104, located most distally along cuff 110, can be used for delivering LF therapeutic stimulation for providing a cardiac therapy. A second pair of electrodes 106 and 108, spaced proximally from distal electrodes 102 and 104, are used for delivering a HF blocking stimulation.

When implanted along the vagus nerve, the distal electrode pair 102 and 104 is positioned more cranially, i.e. closer to the head, than the proximal electrode pair 106 and 108. In this way, the LF therapeutic stimulation delivered to activate cardiac branches of the vagus nerve are delivered using the more cranially positioned electrodes 102 and 104. A higher frequency blocking stimulation delivered using the more distal electrodes 106 and 108 will act to block activation of non-cardiac nerve fibers but allow the low frequency stimulation-induced activation to propagate down the vagus nerve toward the cardiac branch.

Nerve cuff 110 is coupled to a lead body 112, which carries conductors for electrically coupling electrodes 102 through 108 to the IMD 10. While electrodes 102 through 108 are shown positioned along a single nerve cuff 110, it is recognized that separate nerve cuffs, carried by one single or two separate lead bodies or a bifurcated lead body, may be provided for positioning the cardiac therapy electrodes 102 and 104 and the blocking electrodes 106 and 108 at desired locations along the vagus nerve.

In one embodiment, cuff 110 is positioned along the left or right vagus nerve approximately along the C5-C6 cervical vertebrae. This level is relatively easy to access surgically, however it is recognized that other placements of cuff 110 could be used for achieving effective cardiac branch activation and blocking of non-cardiac branches.

In other embodiments, the more cranially positioned electrode pair 102 and 104 may be selected for delivering HF blocking stimulation and the lower electrode pair 106 and 108 may be selected for delivering the LF therapeutic stimulation. Some vagus nerve stimulation therapies may be delivered for treating neurological or psychiatric disorders. When the low frequency activation stimulation is intended to propagate in a cranial direction, the HF blocking stimulation may be delivered more cranially than the LF therapeutic stimulation.

In the above examples, the HF blocking stimulation electrode pair is described as being located more distally along a nerve than the LF therapeutic stimulation electrode pair. Embodiments described herein, however, are not limited to the HF blocking electrode pair being spaced apart distally from the LF stimulation electrode pair, in the direction of the intended activation propagation (efferent activation). Effective blocking of non-targeted nerve branches may be achieved when the HF blocking stimulation electrode pair is spaced apart proximally from the LF stimulation electrodes, in the direction opposite the intended activation propagation toward a targeted tissue. In still other embodiments, a single electrode pair may be used for delivering the LF therapeutic stimulation and the HF blocking stimulation simultaneously or in an alternating manner as described below in conjunction with FIG. 11. It is recognized that blocking of both efferent and afferent nerve branches may be achieved.

Figure 3B:
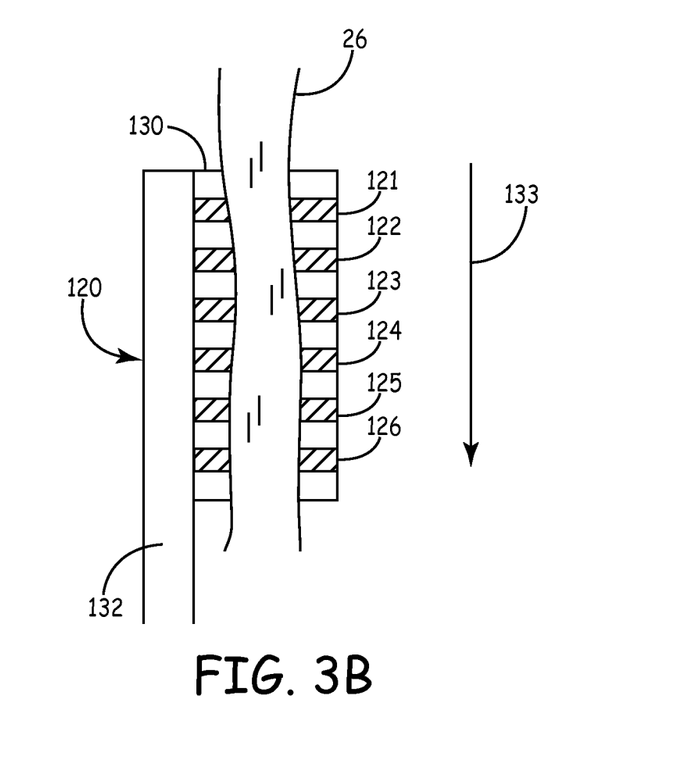
FIG. 3B is an open view of an alternative embodiment of a nerve cuff lead positioned along the vagus nerve.

FIG. 3B is an open view of an alternative embodiment of a nerve cuff lead 120 positioned along the vagus nerve 26. Lead 120 includes a nerve cuff 130 coupled to lead body 132. Arrow 133 indicates the intended activation wavefront propagation in response to LF stimulation pulses. Six electrodes 121, 122, 123, 124, 125 and 126 are mounted along nerve cuff 130 and coupled to electrical conductors extending through lead body 112 for electrical connection to an IMD. Any of electrodes 121 through 126 may be selected in a LF stimulation electrode pair with any of the remaining electrodes used for delivering HF blocking stimulation. In one embodiment, the center two electrodes 123 and 124 are selected for delivering LF therapeutic stimulation and the outer two pairs of electrodes 121,122 and 125, 126 are used for delivering HF blocking stimulation.

Alternatively, any single pair of electrodes, for example 123 and 124, may be selected for delivering both the LF therapeutic stimulation the HF blocking stimulation. Electrode pairs selected for LF therapeutic stimulation and HF blocking stimulation are not necessarily limited to pairs of immediately adjacent electrodes.

Figure 4:
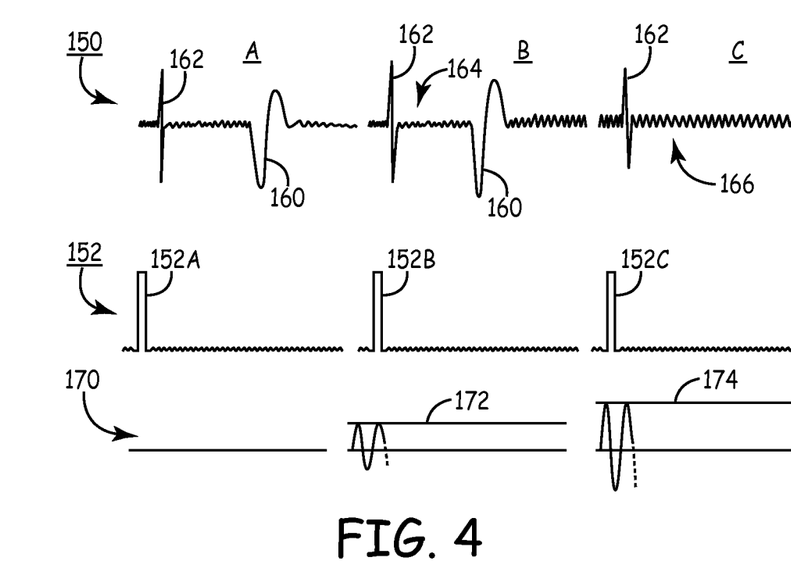
FIG. 4 is an illustrative recording of vagus nerve stimulation and a corresponding laryngeal response.

FIG. 4 is an illustrative recording of vagus nerve stimulation and a corresponding laryngeal response. A laryngeal EMG 150 was recorded during simultaneous delivery of a low frequency train of pulses 152 and high frequency AC stimulation 170. In the particular example shown, the pulse train 152 is delivered at a frequency of 2 Hz, pulse amplitude 3 V, and pulse width 0.5 ms. The LF stimulation is delivered to cause a beneficial slowing of the heart's sinus rhythm. It is noted that only a single pulse 152A, 152B, or 152C of the 2 Hz pulse train is shown in each of panels A, B, and C, respectively. As can be seen in panel A, when the 2 Hz pulse 152A is delivered with no high frequency AC stimulation 170 (shown as a flat baseline), excitation of the laryngeal musculature is seen at 160 following a stimulation artifact 162 caused by the stimulation pulse 152A. The pulse 152A causes activation 160 of the laryngeal musculature, potentially causing adverse side effects during vagal nerve stimulation therapy.

In panel B, HF AC stimulation 172 (represented schematically) is delivered concurrently with the 2 Hz pulse train 152. The HF AC stimulation 172 can be seen as increased baseline noise 164 on the EMG signal 150. In this example, the HF AC stimulation is delivered as a 5 kHz sinusoidal waveform having a 1 Volt peak amplitude. The laryngeal activation 160 is still present in response to the 2 Hz pulse 152B.

In panel C, the amplitude of the HF AC stimulation 174 (represented schematically) is increased to 2 Volt and can be seen as a further increase in the amplitude of baseline noise 166 in the EMG signal 150. The HF AC stimulation delivered at 2 Volts, 5 kHz is effective at blocking the laryngeal response. No laryngeal activation is present after the 2 Hz pulse 152C and corresponding stimulation artifact 162.

The HF stimulation delivered simultaneously with the LF therapeutic stimulation pulse train effectively blocks undesired activation of the laryngeal nerve fibers in the vagus nerve. The efferent vagal nerve fibers innervating the larynx are large type A fibers. The efferent vagal nerve fibers innervating the cardiac sinus node presumed to be responsible for sinus rate slowing that occurs with vagal nerve stimulation are believed to be smaller type B fibers. This observation suggests that the high frequency stimulation blocking effect may be related to differences in nerve fiber size. The high frequency stimulation can be delivered to block excitation of large nerve fibers without affecting the excitability of small nerve fibers. As such, in an autonomic nerve, a therapeutic stimulation therapy can include LF stimulation pulses delivered to activate small nerve fibers innervating a targeted tissue and a HF stimulation waveform for simultaneously blocking large nerve fibers to reduce or eliminate undesired activation of other, non-targeted, excitable tissue. Other therapy applications may include vagal nerve stimulation targeted to affect portions of the brain or central nervous system or stimulation of autonomic nerves innervating the digestive system.

The high frequency stimulation may be delivered using sinusoidal waves, square waves or other wave shapes. The amplitude and frequency at which effective blocking occurs may vary between patients, electrode placement, and other factors. In one embodiment, the HF blocking stimulation is delivered to block activation propagation along efferent nerve fibers that would otherwise conduct activation wavefronts in the same direction as the targeted, activated efferent nerve fibers. This HF blocking method is in contrast to "blocking" stimulation delivered to create uni-directional activation wavefronts. In the later case, the "blocking" stimulation is achieved using carefully controlled wave shapes delivered at physiological frequencies to cathode and anode electrodes that are spaced at specific distances. The stimulation pulse waveform and cathode-anode spacing is designed to cause hyperpolarization of the nerve cells at the anode at approximately the same time that a depolarization originating at the cathode would be propagating past the anode electrode. The hyperpolarized tissue thereby "blocks" further propagation of the depolarization. This type of blocking does not involve the use of high frequency stimulation. The stimulation pulses or wave shapes are generally delivered at a physiological frequency, e.g., on the order of 10 to 50 Hz, and the blocking is achieved at the anode through proper anode positioning with respect to the cathode and carefully controlled wave shapes. In contrast, the high frequency blocking stimulation described herein is not dependent on electrode spacing, may use the same or different bipolar electrode pairs, and blocks both intrinsic and evoked depolarizations from conducting along a nerve branch by maintaining the nerve cells in an artificially induced state of "refractoriness", i.e. a state that prevents depolarization from occurring without hyperpolarizing the cells. The cells are not in a hyperpolarized state during HF stimulation.

In uni-directional activation, the hyperpolarization at the anode must be carefully timed relative to the depolarization at the cathode. In contrast, the cyclical timing of the high frequency stimulation described herein can be delivered without timed relation to a given therapeutic stimulation pulse. The HF blocking stimulation and the LF therapeutic stimulation are delivered simultaneously, but no synchronization between a given HF cycle and a LF pulse is required to achieve a blocking effect of non-targeted nerve fibers. In other words, a LF therapeutic stimulation pulse can occur at any time during a HF stimulation cycle, and the HF stimulation will still cause effective blocking of depolarization of the non-targeted nerve fibers. Since the blocking effect achieved with HF stimulation is independent of interelectrode spacing and relative timing between the HF stimulation cycles and the LF therapeutic stimulation pulses, the delivery of the HF blocking stimulation and LF therapeutic stimulation is easier to control than methods that rely on carefully timed and spaced hyperpolarization required to achieve blocking of a specific depolarization wavefront during therapeutic stimulation at physiological frequencies.

Figure 5:
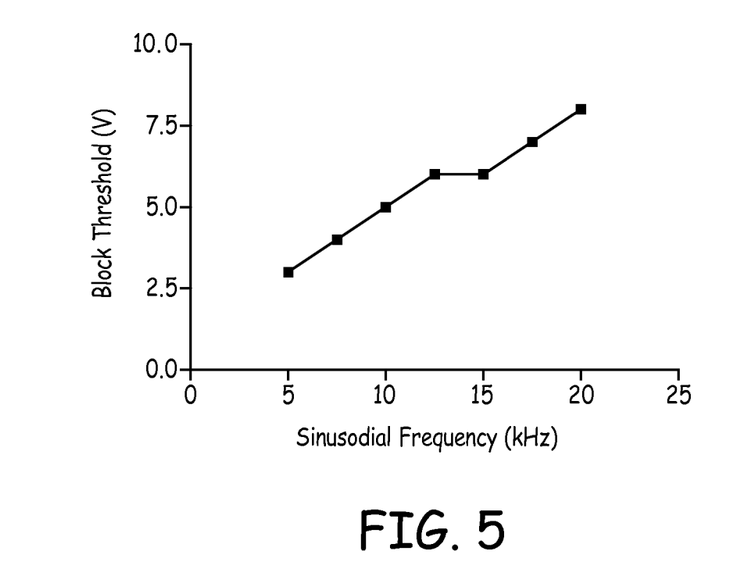
FIG. 5 is a graph of the high frequency blocking stimulation frequency, shown in kHz, versus blocking threshold amplitude in one subject.

FIG. 5 is a graph of the HF blocking stimulation frequency, shown in kHz, versus blocking threshold amplitude in one subject. The blocking threshold is the lowest amplitude at which effective blocking occurs for a given stimulation frequency. The blocking threshold is shown in volts and is seen to increase with increasing frequency of a sinusoidal waveform. Generally, once the frequency is high enough to not cause activation, the amplitude required to cause blocking of nerve activation increases with further increases in frequency. In order to conserve IMD battery charge, a relatively low amplitude, e.g., at or slightly above the blocking threshold, is used at a selected frequency to achieve the blocking effect. In order to minimize the amplitude required, the frequency of the blocking stimulation is selected near the low end of the high frequency range at which effective blocking occurs.

Figure 6:
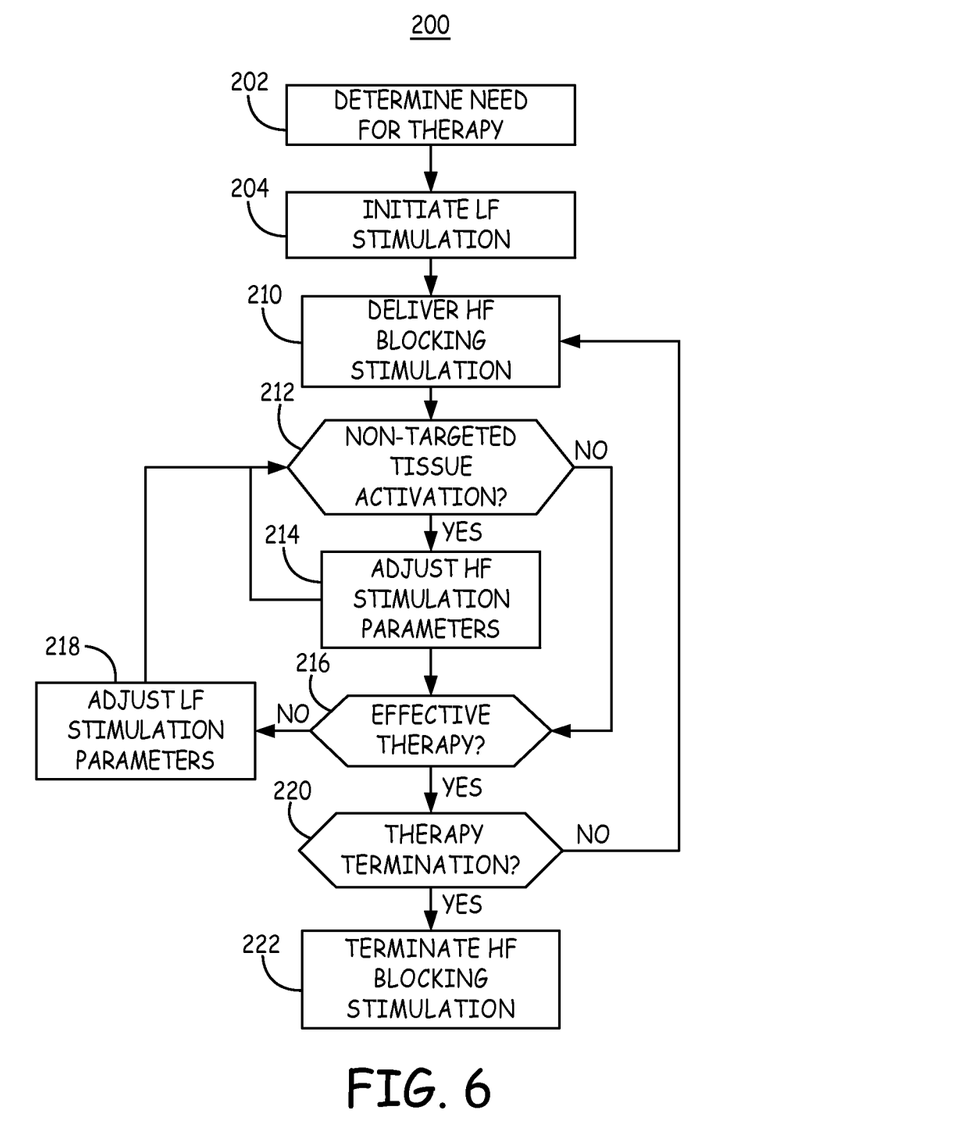
FIG. 6 is a flow chart of one method for delivering vagal stimulation.

FIG. 6 is a flow chart of one method for delivering vagal stimulation. Method 200 is intended to illustrate the functional operation of the device, and should not be construed as reflective of a specific form of software or hardware necessary to practice method 200 and other methods described herein. It is believed that the particular form of software will be determined primarily by the particular system architecture employed in the device and by the particular detection and therapy delivery methodologies employed by the device. Providing software to accomplish the described functionality, in the context of any modern implantable medical device given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 202, a need for delivering an autonomic nerve stimulation therapy is determined. This determination may be made based on physiological signals sensed by the IMD or in response to a command received by an external device, such as a clinician programmer or a patient handheld device. In one embodiment, a need for vagal stimulation is determined based on a monitored heart rate, heart rate variability, hemodynamic monitoring or other cardiac monitoring.

At block 204, the IMD begins delivering a LF therapeutic stimulation intended to activate efferent nerve fibers innervating a targeted excitable tissue. In the above example, vagus nerve stimulation is delivered to provide a therapeutic cardiac effect. LF therapeutic stimulation parameters may vary between embodiments and may be tailored according to individual patient need. For example, a pulse train including a series of monophasic pulses, biphasic pulses or other wave shapes may be delivered at a relatively low frequency, for example less than 5 Hz, and at a pulse amplitude determined to provide activation of desired nerve branches, e.g., the cardiac branches of the vagus nerve. In one embodiment, the LF therapeutic stimulation is delivered to beneficially slow a fast sinus heart rate.

At block 210, relatively higher frequency stimulation is delivered simultaneously with the LF therapeutic stimulation. In the application of a cardiac therapy, the HF stimulation is delivered at a frequency and amplitude expected to block activation of non-cardiac branches of the vagus nerve, particularly the laryngeal nerve fibers. The HF stimulation is delivered during the LF therapeutic stimulation delivery but without adversely impacting the effectiveness of the cardiac therapy. The HF blocking stimulation may be delivered as a sinusoidal wave, square wave or other wave shape. The frequency of the blocking stimulation may vary between embodiments but is expected to be greater than approximately 1 kHz and may be as high as 20 kHz or more. The frequency is at least greater than a maximum frequency at which nerve fiber activation occurs regardless of pulse amplitude. The amplitude required to achieve effective blocking will increase with frequency and is therefore selected depending on the particular frequency of the HF stimulation waveform.

In some embodiments, the HF blocking stimulation applied at block 210 may be set to a default frequency and amplitude known to effectively block activation of non-targeted branches or fibers of the autonomic nerve being stimulated. Alternatively, the HF blocking stimulation may be set at a programmed or nominal value and the activation of a non-targeted tissue may be monitored at block 212 to allow adjustment of high frequency stimulation parameters at block 214.

For example, laryngeal activation may be monitored manually during LF vagal nerve stimulation intended to have a cardiac benefit. Laryngeal activation may be monitored at block 212 manually by palpation of the larynx. A clinician may then use an external device to reprogram HF stimulation parameters until laryngeal activation disappears. Laryngeal activation may be perceived by the patient allowing the patient to respond using an external device to send a command to cause the IMD to adjust the HF blocking stimulation amplitude or frequency.

Non-targeted tissue activation may alternatively be monitored automatically by the IMD using, for example, EMG sensing electrodes, an accelerometer or other motion sensor, a microphone or other acoustical sensor, or any other sensor generating a signal responsive to non-targeted tissue activation. A sensing window may be set to facilitate detection of an evoked signal following delivery of a therapeutic stimulation pulse as shown in FIG. 4.

If an activation signal is present in a timed relation to a LF stimulation pulse, the HF stimulation parameters may be adjusted at block 214 until the evoked activation signal is no longer present. The amplitude may be increased (e.g., up to some predetermined maximum) or the frequency may be decreased (e.g., down to some predetermined minimum). If other electrodes are available, a different electrode pair may be selected for delivering the blocking stimulation.

At block 216, physiological sensing or clinical evaluation may be performed to determine if the LF stimulation is effective. For example, the heart rate may be monitored to determine if a heart rate has slowed in response to vagal stimulation. If the LF therapeutic stimulation is not achieving a desired effect, as determined at block 216, the LF stimulation parameters may be adjusted at block 218. This adjustment may include selecting a new amplitude, frequency, or LF stimulation electrode pair.

Adjustment of the LF therapeutic stimulation may require adjustment of the HF blocking stimulation. For example, if a new LF stimulation electrode pair is selected, the HF blocking stimulation electrode pair may need to be changed. A HF stimulation electrode may be reassigned as a LF stimulation electrode to allow more therapeutically effective LF stimulation. Alternatively, the relative locations of the LF and HF stimulation electrodes may be altered if a new LF stimulation pair is selected. A different HF stimulation electrode pair may then be desired to maintain a positional relationship between the electrodes delivering LF stimulation and the electrodes delivering HF stimulation.

After adjusting LF stimulation parameters, method 200 may return to block 212 to verify that non-targeted tissue activation is not occurring. Changing the LF stimulation parameters may result in ineffective blocking stimulation. For example, if a new LF stimulation electrode pair was selected at block 218, requiring a change in the HF blocking stimulation electrode pair, a different amplitude or frequency may be required to cause effective blocking using the new HF stimulation electrodes.

Once effective blocking stimulation is established as evidenced by the absence of detectable non-targeted tissue activation, the blocking stimulation may be maintained as long as the LF stimulation therapy is delivered. If the therapy is being terminated, as determined at block 220, the HF blocking stimulation is also terminated at block 222. The LF stimulation therapy may be terminated for a number of reasons including a reversal of the condition detected which caused the therapy to be initiated, receipt of a command transmitted to the IMD by an external device, or expiration of a predetermined therapy delivery time interval.

It is recognized that HF blocking stimulation may not be required at all times that a LF therapeutic stimulation is being delivered. For example, the alleviation of some side effects caused by activation of non-targeted tissues, such as voice alteration caused by laryngeal activation, may not be required while a patient is sleeping. In some embodiments, therefore, the HF blocking stimulation may be programmed to occur only when the LF therapeutic stimulation is being delivered during particular hour of the day or night or according to other criteria.

The onset of the blocking effect of the high frequency stimulation may take up to one second or more to occur, and the blocking effect may disappear up to one second or more after HF stimulation is terminated. As such, the HF blocking stimulation may be initiated prior to initiating the LF therapeutic stimulation and may terminate prior to terminating the LF therapeutic stimulation.

Figure 7:
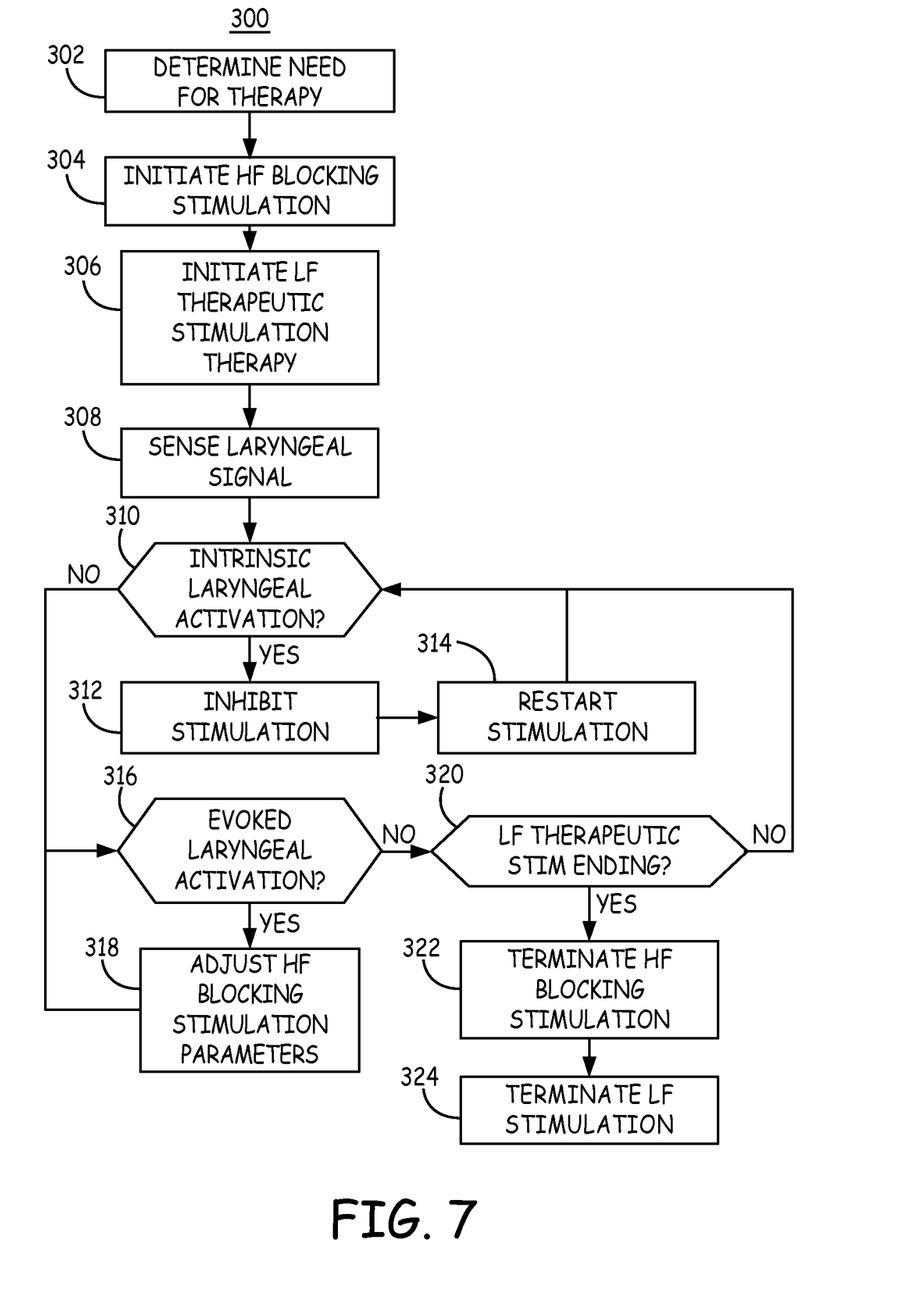
FIG. 7 is a flow chart of another method for delivering a vagus nerve stimulation therapy.

FIG. 7 is a flow chart of a method 300 for delivering a vagus nerve stimulation therapy, which may also be applicable to other autonomic nerve stimulation therapies. At block 302, a need for delivering the vagus nerve stimulation therapy is determined as generally described above. At block 304, HF blocking stimulation is initiated. At block 306, the LF therapeutic stimulation is initiated after a short delay following the onset of the HF blocking stimulation. The blocking effect may not occur immediately upon initiating of the HF blocking stimulation. For example, the nerve block may appear after about one second after the HF stimulation is started. As such, the LF therapeutic stimulation is initiated after a short delay to allow the HF blocking stimulation to take effect and thereby reduce the likelihood of an early LF stimulation pulse causing activation of non-targeted excitable tissue.

At block 308, a laryngeal signal is sensed to monitor activations of the laryngeal muscles. A laryngeal signal may be, but is not limited to, an EMG signal, an accelerometer or other motion sensor signal, or a microphone or other acoustical sensor signal. Intrinsic and/or evoked activations may be monitored as indicated at blocks 310 and 316. Intrinsic laryngeal activation may be detected at block 310, for example, when a patient is attempting to speak or cough. Blocking stimulation delivered to either the left or the right vagus nerve is not expected to have significant adverse effects on the normal use of the larynx. If normal use of the larynx is impaired or altered in any way by the blocking stimulation, however, the HF blocking stimulation may be temporarily inhibited at block 312 whenever intrinsic laryngeal activity is detected to allow normal intrinsic activations to take place.

Figure 8:
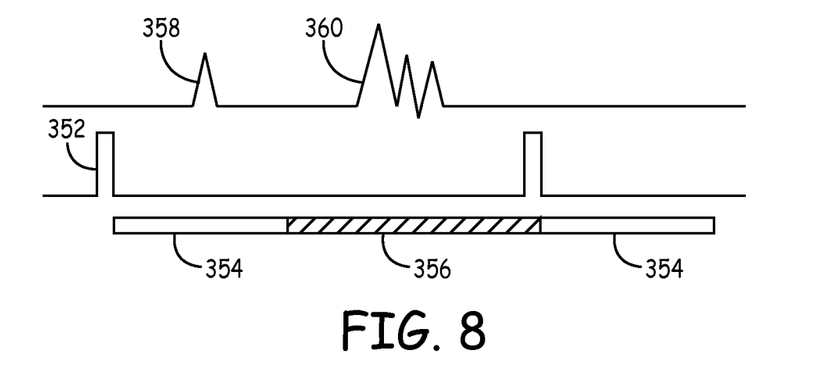
FIG. 8 is a diagram of a low frequency stimulation pulse followed by an evoked response sensing window and an intrinsic activity sensing window.

Intrinsic laryngeal activation detected at block 310 can be identified as signals lacking a timed relationship to the LF therapeutic stimulation pulses. FIG. 8 is a diagram of a LF stimulation pulse 352 followed by an evoked response sensing window 354 and an intrinsic activity sensing window 356. A laryngeal activation 358 detected within a predetermined time period following stimulation pulse 358, defined by window 354, would be detected as an evoked response to the pulse 352. Activations 360 occurring outside evoked response sensing window 354, i.e. within intrinsic activity sensing window 356, are detected as intrinsic activations.

Referring again to FIG. 7, if intrinsic activations are detected, stimulation may be temporarily inhibited at block 312 and then restarted at block 314. The HF blocking stimulation may be inhibited to allow normal use of the larynx. Alternatively, both the LF therapeutic stimulation and the HF blocking stimulation may be inhibited at block 312 to avoid undesired laryngeal activation in response to the LF stimulation pulses when the HF blocking stimulation is inhibited. For example, intrinsic activations associated with attempts to speak may cause both HF and LF stimulation to be temporarily suspended to allow the patient to speak without voice alteration. While not explicitly shown, it is recognized the temporary stimulation inhibition could be initiated manually by a patient using a hand-held device capable of telemetric communication with the IMD, finger tapping on the IMD, or other user-IMD communication method.

At block 316, sensing for evoked activations associated with the LF stimulation pulses is performed. If evoked activations are detected, the HF blocking stimulation parameters may be adjusted at block 318 as generally described above. If no laryngeal activations are occurring, the LF therapeutic stimulation is maintained at the currently selected stimulation parameters for a therapy delivery duration.

At block 320, a determination is made when the LF therapeutic stimulation is ending. The HF blocking stimulation may be terminated at block 322 just prior to terminating the LF therapeutic stimulation at block 324. The blocking effect may disappear after a short delay following termination of the HF stimulation. As such, the HF stimulation may be terminated slightly earlier than the LF stimulation to conserve IMD battery charge.

Figure 9:
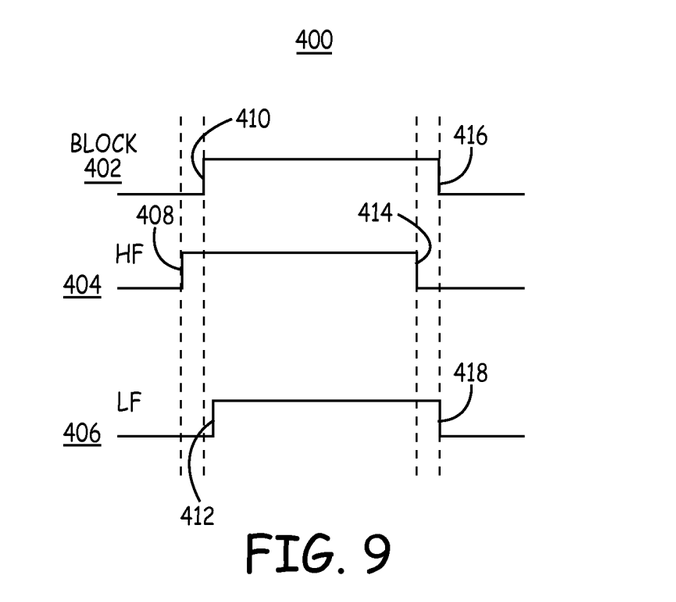
FIG. 9 is a timing diagram illustrating the staggered initiation and termination of the high frequency blocking stimulation and the low frequency therapeutic stimulation.

FIG. 9 is a timing diagram 400 illustrating the staggered initiation and termination of the HF blocking stimulation and the LF therapeutic stimulation. The blocking effect 402 is shown in timed relationship to the HF blocking stimulation 404 and the LF therapeutic stimulation 406. HF blocking stimulation is initiated at 408. The onset 410 of blocking effect 402 is slightly delayed in time after the initiation 408 of HF stimulation 404. Accordingly, the onset 412 of LF therapeutic stimulation 406 may be delayed after the initiation 408 of HF stimulation 404 to avoid an early activation of non-targeted tissue prior to the appearance of effective blocking.

The HF stimulation 404 is terminated at 414. The blocking effect disappears at 416, slightly lagging HF stimulation termination 414. As such, HF blocking stimulation 404 may be terminated at 414 slightly before the termination 418 of LF stimulation 406. When the HF blocking stimulation termination 416 is properly timed relative to the LF therapeutic stimulation termination 418, the blocking effect 402 will persist through the end of the LF stimulation 406 while allowing early termination of the HF stimulation 404 to conserve battery charge.

Figure 10:
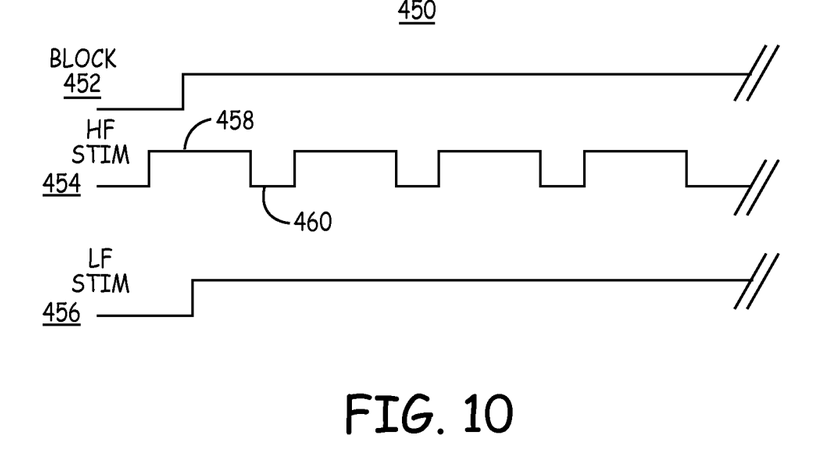
FIG. 10 is a timing diagram illustrating intermittent high frequency blocking stimulation delivered to maintain a continuous blocking effect during continuous low frequency therapeutic stimulation.

FIG. 10 is a timing diagram 450 illustrating intermittent HF blocking stimulation 454 delivered to maintain a continuous blocking effect 452 during continuous LF therapeutic stimulation 456. The blocking effect of HF stimulation disappears after a short delay, for example 1 second, after the HF stimulation is terminated. As such, a continuous blocking effect 452 can be achieved with properly timed intermittent intervals of HF blocking stimulation 454.

The HF blocking stimulation 454 is shown to be delivered in "bursts" 458 separated by short intervals of no stimulation 460. Blocking stimulation 454 is cycled on and off with an "on" duration 458 separated by "off" duration 460. The "off" duration or inter-burst interval 460 is short enough to prevent the blocking effect from disappearing before the next "on" duration or burst 458 starts. In this way, continuous blocking effect 452 is achieved while conserving IMD battery charge. The on/off duty cycle of the intermittent HF stimulation 454 may vary between embodiments, but may be optimized to achieve the minimum "on" time required to maintain continuous blocking effect 452.

Figure 11:
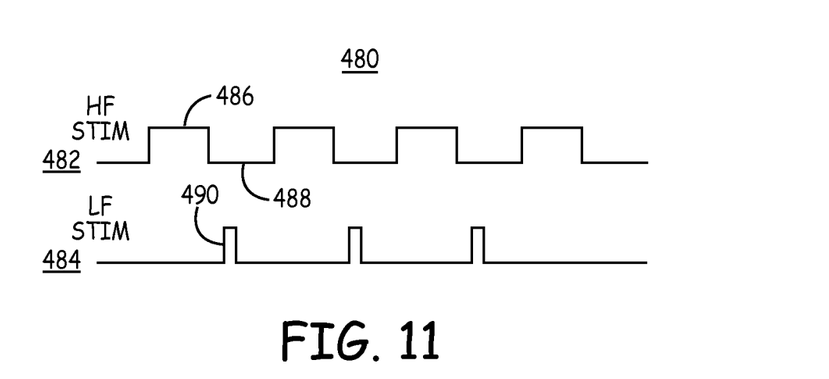
FIG. 11 is a timing diagram of yet another embodiment for delivering simultaneous low frequency therapeutic stimulation and high frequency blocking stimulation.

FIG. 11 is a timing diagram of yet another embodiment for delivering simultaneous LF therapeutic stimulation 484 and HF blocking stimulation 482. The LF stimulation pulses 490 may be delivered during intervals 488 between bursts 486 of HF stimulation 482. HF blocking stimulation 482 is shown as intermittent stimulation for achieving a continuous blocking effect as described above in conjunction with FIG. 10. If the same electrode pair is being used to deliver both the HF blocking stimulation 482 and the LF stimulation 484, it may be desirable to deliver the LF stimulation pulses 490 during inter-burst intervals 488, for example to allow switching circuitry to couple the electrode pair to different LF pulse generator and HF signal generator outputs of a therapy delivery module.

While embodiments described herein relate to the delivery of a vagal stimulation including a cardiac activating stimulation portion and a non-cardiac blocking stimulation portion, it is recognized that the concepts presented herein relating to coordinated delivery of high frequency blocking stimulation and lower frequency, therapeutic activation stimulation are not necessarily limited to cardiac therapy applications and may be applied to other therapeutic applications.

Thus, methods and associated apparatus for delivering autonomic nerve stimulation have been presented in the foregoing description with reference to specific embodiments. It is appreciated that various modifications to the referenced embodiments may be made without departing from the scope of the invention as set forth in the following claims.

The invention claimed is:

1. An implantable medical device for electrically stimulating an autonomic nerve, comprising;
   an electrode pair adapted for positioning along the autonomic nerve;
   a therapy delivery module coupled to the electrode pair, the therapy delivery module comprising
      an electrical stimulation pulse generator for delivering stimulation pulses at a first frequency to the autonomic nerve via the electrode pair;
      a high frequency signal source for delivering a high frequency electrical signal at a second frequency higher than the first frequency to the autonomic nerve via the electrode pair; and
   a control module configured to control the therapy delivery module to deliver the first frequency stimulation pulses to excite a target tissue innervated by the autonomic nerve and deliver the high frequency signal during the first frequency stimulation pulse delivery; and
   wherein the pulse generator and the high frequency signal source are coupled to the electrode pair.

2. The device of claim 1 further comprising:
   a first sensor generating a signal corresponding to activation of a non-targeted tissue innervated by the autonomic nerve;
   the control module receiving the first sensor signal and adjusting the high frequency electrical signal delivered by the therapy module in response to the first sensor signal.

3. The device of claim 1 further comprising a first sensor generating a signal corresponding to a response of the targeted tissue to the first frequency stimulation pulses, the control module receiving the second sensor signal, adjusting the delivery of the first frequency stimulation pulses in response to the first sensor signal, and adjusting the delivery of the high frequency electrical signal in response to the adjustment of the first frequency stimulation pulse delivery.

4. The device of claim 1 wherein the control module initiates the delivery of the high frequency electrical signal and initiates the delivery of the first frequency stimulation pulses after a delay following the high frequency electrical signal initiation.

5. The device of claim 1 wherein the control module terminates the delivery of the high frequency electrical signal and terminates the delivery of the first frequency stimulation pulses after a delay following the high frequency electrical signal termination.

6. The device of claim 1 wherein the control module controls the therapy delivery module to deliver intermittent bursts of the high frequency electrical signal during the first frequency stimulation pulse delivery.

7. The device of claim 6 wherein the therapy delivery module delivers the pulses at the first frequency during intervals between the bursts of the high frequency electrical signal.

8. A method for delivering electrical stimulation to an autonomic nerve for use in an implantable medical device, comprising:
   delivering electrical stimulation pulses at a first frequency to an autonomic nerve;
   delivering a high frequency electrical signal at a second frequency higher than the first frequency to the autonomic nerve during the first frequency stimulation pulse delivery; and
   wherein the first frequency stimulation pulses and the high frequency signal are delivered using a same electrode pair.

9. The method of claim 8 further comprising:
   sensing a signal corresponding to activation of a non-targeted tissue innervated by the autonomic nerve; and
   adjusting the high frequency electrical signal in response to a first sensor signal.

10. The method of claim 8 further comprising:
    sensing a signal corresponding to a response of the targeted tissue to the first frequency stimulation pulses;
    adjusting the delivery of the first frequency stimulation pulses in response to a first sensor signal; and
    adjusting the delivery of the high frequency electrical signal in response to the adjustment of the first frequency stimulation pulse delivery.

11. The method of claim 8 further comprising:
    initiating the high frequency stimulation signal delivery; and
    initiating the delivery of the first frequency stimulation pulses after a delay following the initiation of the high frequency electrical signal.

12. The method of claim 8 further comprising:
    terminating the delivery of the high frequency electrical signal; and
    terminating the delivery of the first frequency stimulation pulses after a delay following the high frequency stimulation signal termination.

13. The method of claim 8 wherein the high frequency stimulation signal delivery comprises delivering intermittent bursts of the high frequency electrical signal during the first frequency stimulation pulse delivery.

14. The method of claim 13 wherein delivering the first frequency stimulation pulses comprises delivering the stimulation pulses during an interval between the bursts of the high frequency electrical signal.

\* \* \* \* \*